(12) United States Patent
Weibel et al.

(10) Patent No.: US 10,413,672 B2
(45) Date of Patent: Sep. 17, 2019

(54) DISPENSING DEVICE WITH SELECTABLE FLOW CHANNELS AND SEAL

(71) Applicant: WEIBEL CDS AG, Waldstatt (CH)

(72) Inventors: Ludwig Daniel Weibel, Waldstatt (CH); Christoph Egloff, Löhningen (CH)

(73) Assignee: Weibel CDS AG, Waldstatt (CH)

( * ) Notice: Subject to any disclaimer, the term of this patent is extended or adjusted under 35 U.S.C. 154(b) by 246 days.

(21) Appl. No.: 15/502,833

(22) PCT Filed: Aug. 14, 2014

(86) PCT No.: PCT/EP2014/067435
§ 371 (c)(1),
(2) Date: Feb. 9, 2017

(87) PCT Pub. No.: WO2016/023590
PCT Pub. Date: Feb. 18, 2016

(65) Prior Publication Data
US 2017/0232200 A1    Aug. 17, 2017

(51) Int. Cl.
*A61M 5/00* (2006.01)
*A61M 5/31* (2006.01)
(Continued)

(52) U.S. Cl.
CPC ........ *A61M 5/3134* (2013.01); *A61M 3/0279* (2013.01); *A61M 5/1782* (2013.01);
(Continued)

(58) Field of Classification Search
CPC .. A61M 2005/3114; A61M 2005/3118; A61M 2005/3128; A61M 2209/045;
(Continued)

(56) References Cited

U.S. PATENT DOCUMENTS 2,261,213 A    11/1941  Bierman
2007/0088282 A1*  4/2007  Ranalletta ............. A61M 5/204
                                                        604/184

(Continued)

FOREIGN PATENT DOCUMENTS

EP    0 814 866 B1    6/2001
EP    1 755 520 B1    1/2012
(Continued)

OTHER PUBLICATIONS

International Search Report Corresponding to PCT/EP2014/067435 dated Apr. 8, 2015.
(Continued)

*Primary Examiner* — Rebecca E Eisenberg
(74) *Attorney, Agent, or Firm* — Michael J. Bujold (57) ABSTRACT

A dispensing device (1) for dispensing a fluid, preferably an injection syringe. The device comprises a main body (2) which has a longitudinal axis (A) and has a receiving space (3) for receiving the fluid, and a connection channel (4) communicates with the receiving space. The connection channel opens on a valve face (5) of the main body. The device comprises a movable flow control element (6) arranged on the main body. The flow control element has one or more flow channels (7) which open on a valve face (8) of the flow control element. The connection channel of the main body and the flow channels of the flow control element are fluidically connected to each other by relative movement of main body and flow control element. A sealing element (10) is arranged between the valve face of the main body and the valve face of the flow control element.

20 Claims, 8 Drawing Sheets

(51) Int. Cl.
*A61M 5/178* (2006.01)
*A61M 5/20* (2006.01)
*A61M 5/32* (2006.01)
*A61M 39/22* (2006.01)
*A61M 3/02* (2006.01)
*A61M 5/34* (2006.01)

(52) U.S. Cl.
CPC .......... *A61M 5/204* (2013.01); *A61M 5/3202* (2013.01); *A61M 5/34* (2013.01); *A61M 39/22* (2013.01); *A61M 39/223* (2013.01); *A61M 2005/3114* (2013.01); *A61M 2005/3118* (2013.01); *A61M 2005/3128* (2013.01); *A61M 2209/045* (2013.01)

(58) Field of Classification Search
CPC .. A61M 39/22; A61M 39/223; A61M 3/0279; A61M 5/3134; A61M 5/3202; A61M 5/34
See application file for complete search history.

(56) References Cited

U.S. PATENT DOCUMENTS

| | | | |
|---|---|---|---|
| 2014/0131389 A1* | 5/2014 | Weibel | B65D 47/205 |
| | | | 141/2 |
| 2014/0305527 A1 | 10/2014 | Weibel | |
| 2015/0367083 A1* | 12/2015 | Weibel | A61M 5/31 |
| | | | 604/198 |

FOREIGN PATENT DOCUMENTS

| | | |
|---|---|---|
| EP | 2 744 468 B1 | 6/2015 |
| WO | 2007/041512 A2 | 4/2007 |

OTHER PUBLICATIONS

Written Opinion Corresponding to PCT/EP2014/067435 dated Apr. 8, 2015.

* cited by examiner

DISPENSING DEVICE WITH SELECTABLE FLOW CHANNELS AND SEAL

The present invention relates to a injection syringe for dispensing a fluid, in particular for medical use, according to the preamble of claim 1.

Using syringes to inject patients with liquid formulations of pharmaceutical ingredients is widely known. However, syringes are also used in the clinical environment, for example to transfer liquids between two containers or from a container to a catheter. Nowadays, for reasons of hygiene, in this connection these are mostly disposable syringes which have to be filled with the liquid to be dispensed before use, in this case, the utmost care must be taken to safeguard sterility, which is difficult to guarantee, in particular where medication is self-dispensed by a patient.

In order to deal with this problem, pre-filled syringes are known where a medication is already pre-filled into the dispensing volume of the syringe. These types of syringes, however, have certain disadvantages as regards their storage. For example, a piston rod, by way of which a piston is slidable in the syringe, has to be completely extended. The storage of the syringe in the filled state consequently takes up a comparatively large amount of space and precautions have to be taken so that the piston rod, which sticks out a long way, is not unintentionally actuated.

In addition, the storage of pharmaceutical ingredients in solution is often problematic and in many cases is not even practically possible. Problems exist, in this case, along with the possible ability of an active substance to decompose in solution, in unwanted interactions between the materials of the syringe and the liquid formulation. Thus, in particular, a problem arises due to contact between the liquid and the sealing materials and lubricants, which are necessary so that the piston can easily be slid even after being stored for a fairly long time in the syringe body. Contamination of the solution contained in the syringe can lead to the regulatorily fixed boundaries being exceeded or, in the worst case, even to at least partial decomposition of the pharmaceutical ingredient.

In particular, in the case of active substances which are not storable in solution, it is necessary not to mix different substances with one another or to produce a solution until briefly prior to administration to a patient. In this case, this can be, for example, the reconstitution of a lyophilizate. However, the mixing of two liquids is also conceivable. To this end, the different components have to be stored in separate containers and combined under sterile conditions before they can be transferred into a dispensing device, for example into an injection syringe.

Consequently, there is a need for dispensing devices which are suitable for filling from containers such as, for example, glass vials under the most sterile conditions. These types of devices are described, for example, in EP 0 814 866 B1 or EP 1 755 520 B1. Both documents relate to dispensing devices for liquid pharmaceuticals which are couplable with vials by means of adapter. By means of a flow control device, which essentially fulfils the function of a three-way valve, said vials can, in each case, become fluidically connected, where required, to a receiving space for receiving a fluid inside the dispensing device. The receiving space can be additionally connected to an outlet which, for example, opens out into a further vial or an injection syringe. Reliable administration of a liquid formulation to a patient, occasionally also with reconstitution of a lyophilizate, is possible as a result of the said devices.

A disadvantage of the described systems, however, is that in particular the design of the flow control device is relatively complex, which makes the production thereof difficult, in particular in large quantities, for example as a result of injection molding. The sealing of the flow control device provides a further problem. In order to achieve this to a desired extent, the fluid-conducting parts have to be produced with great precision. In addition, a conical geometry is used in particular for the flow control device within said context, which once again makes the use of lubricants necessary in order to prevent the conical parts from jamming. As already mentioned, the use of lubricants, however, in the case of these types of devices is problematic as such types of lubricant compounds may not only decompose over a longer storage period but the lubricant may also contaminate the formulation. In addition, the achievable sealing is a problem when relatively high pressures occur inside the device when the medication is being dispensed. This can be the case, for example, when dispensing a liquid formulation subcutaneously to a patient, when it is desirable to use as thin a syringe needle as possible in order to make the dispensing as painless as possible for the patient.

It is, consequently, the object of the invention to overcome the disadvantages in the prior art.

In particular, it is an object of the invention to provide a dispensing device for dispensing a fluid that is easy and safe to handle, in a preferred manner for one-off use. The dispensing device is additionally to be usable in a versatile manner and to be simple in design. It is to be suitable for production in large quantities, in particular as a result of injection molding. In addition, it is also to ensure good sealing even at relatively high liquid pressures.

Said objects are achieved by a injection syringe which comprises the features in claim 1. Said device includes, on the one hand, a basic body which has a longitudinal axis (A) and comprises a preferably hollow-cylindrical receiving space for receiving the fluid and a connection channel which communicates with the receiving space. The connection channel opens out, in this case, at a valve face of the basic body. On the other hand, the device includes a flow control element which is arranged on the basic body so as to be movable. Said flow control element comprises one or several flow channels. Said flow channels open out at a valve face of the flow control element.

The valve faces of the basic body and of the flow control element can be arranged parallel to one another. The term parallel, in this case, is to be understood with reference to faces, as a first face being parallel to a second face when each point on the first face is at the same distance from the second face. The distance between a point and a face refers, in this case, to the length of the section, which is delimited by the point and the point of the face closest to it.

The connection channel of the basic body and the flow channels of the flow control element are directly or indirectly fluidically connected to one another or are movable into fluidic connection with one another as a result of a relative movement of the basic body and of the flow control element.

The invention is distinguished in that a sealing element is arranged between the valve face of the basic body and the valve face of the flow control element.

Said design makes it possible to obtain the desired valve effect in a simple manner and to achieve improved reliability. As a result of the presence of a sealing element between the valve faces of the basic body and of the flow control element, considerably better sealing of the device is achieved. This is in particular advantageous when comparatively high pressures occur in the interior of the device. In addition, the presence of a sealing element enables the use of lubricants and/or sealing greases to be omitted. This makes possible a clearly improved storage life of the injection syringe over longer periods. Contamination of the liquid flowing through the device is also excluded by such means. Jamming of parts which move in relation to one another is avoided even after a longer storage period.

In the case of the injection syringe according to the invention, in a preferred manner the valve face on the basic body forms an end face of the basic body. Said design is particularly advantageous as such a injection syringe can manage without curved fluid channels, this means substantially straight fluid channels. This leads to a significant simplification when manufacturing the injection syringe automatically in high quantities, in particular as a result of injection molding. In addition, conical geometry of the valve can be avoided by placing the two valve faces end to end, which makes jamming of the parts which move in relation to one another almost impossible.

The valve faces, in this case, can be planes, wherein the longitudinal axis (A) of the basic body preferably extends perpendicular with respect to said planes. This provides a further simplification of the valve design. In addition, as a result of the, in this case, planar valve design, it is possible to use sealing elements which essentially consist of flat disks produced from an elastic material. Such sealing elements are widespread and can be obtained in diverse variants. This opens up, on the one hand, a large amount of scope when designing the injection syringe according to the invention as the material composition of the sealing element can be adapted to the preparation to be dispensed. As a result, the production costs are also lowered.

The sealing element preferably has a maximum extension of 10 mm in the direction of the longitudinal axis (A) of the basic body. In a preferred manner, said extension is between 3 mm and 1 mm. The sealing element can be made from an elastomer, in particular from a thermoplastics elastomer, natural rubber or a synthetic rubber. Among other things, ethylene-propylene-copolymers, butyl rubbers, polyether amides, epoxy rubbers, urethane rubbers, silicone rubbers or polysulfide rubbers are suitable as synthetic rubbers.

The basic body can advantageously comprise a head piece which directly adjoins the receiving space and is preferably rotationally-symmetrical, in a preferred manner cylindrical or in the form of a truncated cone. As a result of said development of the basic body, the flow control element can be realized as a cap with a receiving means which is fitted onto the head piece. This means, on the one hand, that assembly of the injection syringe is made very simple and efficient. On the other hand, a modular design of the injection syringe can also be realized, where, depending on the intended use, different basic bodies can be combined with different flow control elements.

The flow control element can be movable from a first control position, in which a fluid connection between the connection channel of the basic body and at least one flow channel of the flow control element is interrupted, into at least one further second control position. In said second control position, there can be a fluid connection between the connection channel and a flow channel, which is interrupted in the first control position. In an advantageous embodiment, the flow control element is movable, preferably additionally, from a second type of control position into a first type of control position. As a result, depending on the intended use of the injection syringe, different fluid paths can be opened or closed, as required.

However, the flow control element can also comprise at least one flow channel which is fluidically connected to the connection channel of the basic body irrespective of the control position of the flow control element. This simplifies the design and the method of operation of the injection syringe when no actual valve action is necessary for a flow channel.

The flow control element can comprise at least one flow channel which runs parallel to the longitudinal axis (A) of the basic body at least in the region of its valve face. In addition, the connection channel can also extend on the basic body substantially parallel to the longitudinal axis (A) thereof of the basic body. A injection syringe with such an arrangement of connection channel and flow channels can be produced in a particularly easy and cost-efficient manner.

In a preferred manner, the flow control element on the basic body can be arranged so as to be rotatable about a rotational axis which is substantially parallel to the longitudinal axis (A) of the basic body and the flow control element can be movable as a result of rotation between several control positions. A relative rotational movement, between basic body and flow control element makes it possible to realize the desired, valve action in a simple and space-saving manner. However, in principle, a translatory relative movement of basic body and flow control element, for example as a result of sliding the flow control element in a direction perpendicular to the longitudinal axis (A) of the basic body, would also be conceivable.

The connection channel on the basic body can be arranged eccentrically or also coaxially with reference to the longitudinal axis (A) of the basic body. As a result, in particular where the basic body and the flow control element are realized so as to be rotationally movable, the most varied valve configurations are conceivable.

However, at least one flow channel can also be arranged on the flow control element eccentrically and/or also coaxially with reference to the longitudinal axis (A) of the basic body. An even wider spectrum of valve configurations is also made possible as a result.

A relative movement region of the basic body and the flow control element can be delimited by a delimiting device in such a manner that movement is possible only from a first into a second control position. It is ensured in this way that the user is not able move the flow control element too far, that is to say beyond a second control position.

In addition to the delimiting device, a blocking device can also be present in an advantageous manner on a injection syringe according to the invention, by way of which blocking device the relative movement direction, in particular a rotational direction, of the flow control element in relation to the basic body is preset. In particular, a movement, direction from a first control position into a second control position can be preset. It is ensured in this way that a user cannot move, in particular rotate, the flow control element, for example after a filling operation, in a wrong direction. The blocking device, in this case, can be realized in the manner of a ratchet and on the closure element can include, for example, pawls which are able to engage in a corresponding toothing on the basic body, or the other way around.

The presence of a blocking device in combination with a delimiting device also ensures that the flow control element is locked, for example in a dispensing position, when it has been taken once. The flow control element can consequently no longer be moved into a filling position, thereby preventing multiple use of the injection syringe.

In a preferred manner, on its valve face, the basic body comprises at least one element for preventing a relative rotation of basic body and sealing element. This can avoid the basic body and the sealing element twisting relative to one another, which can result in the connection channel being blocked. The element for preventing a relative rotation of basic body and sealing element, in this case, can be developed, for example, as a mouth connecting piece of the connection channel. In the case of such a realization, the valve face of the basic body must not be altered up to the mouth of the connection channel, for example as a result of an additional anti-rotation device. In addition, said arrangement ensures that the sealing element rests correctly on the valve face of the basic body, in particular in the region of the mouth of the connection channel.

An indirect fluid connection can be producible via the sealing element between the connection channel of the basic body and at least one flow channel of the flow control element. Thus, for example, by means of the sealing element, an indirect fluid connection can be producible on the flow control element between a connection channel, which is arranged coaxially with the longitudinal axis (A) of the basic body, and at least one flow channel which is arranged eccentrically with reference to the longitudinal axis (A) of the basic body. In addition, along with at least one flow channel arranged on the flow control element eccentrically with reference to the longitudinal axis (A) of the basic body, there can be present a further flow channel which is connected to the connection channel of the basic body irrespective of the control position of the flow control element.

As an option, the further flow channel, which is connected to the connection channel of the basic body irrespective of the control position of the flow control element, can be arranged coaxially with the longitudinal axis (A) of the basic body.

However, it is also possible that by means of the sealing element, an indirect fluid connection is producible on the flow control element between a connection channel, which is arranged eccentrically with reference to the longitudinal axis (A) of the basic body, and a flow channel which is arranged coaxially or eccentrically with reference to the longitudinal axis (A) of the basic body.

This illustrates the high level of flexibility of a injection syringe according to the invention with reference to the realizable valve configurations.

In a preferred embodiment of the present invention, the sealing element is compressible as a result of moving the flow control element from a first control, position into a second control position. Such compression, can be effected, in particular, as a result of the distance between the valve face on the basic body and the valve face on the flow control element being reduced, as a result of moving the flow control element. This can be effected, on the basic body, for example, by means of an inclined plane, in particular by means of a thread, as a result of which the flow control element is displaced with a rotation against the basic body. Compression of the sealing element is desirable in particular in order to ensure or increase the sealing action of the sealing element. This can be important, in particular, where a injection syringe according to the invention is stored for a longer period prior to its use.

A cannula, in particular an injection needle or an irrigation cannula, is arranged or arrangeable in such manner on the flow control element that there is a fluid-tight fluid connection to a flow channel, wherein, in a preferred manner, the cannula is fixedly inserted into the flow channel and, in particular, is arranged parallel to the longitudinal axis (A) of the basic body.

The term cannula, in this context, designates a hollow needle with an interior which is realized for guiding a fluid. A cannula relates in the present case, in particular, to an injection needle for introducing (injecting) a medication in a subcutaneous, intervascalar or intermuscular manner into the human or animal body or for removing (tapping) bodily fluids. Likewise, so-called irrigation cannulas are also included, where the fluid can be injected, for example, into existing openings (body cavities) without injuring tissue.

A cannula can be fitted or screwed, for example, onto a corresponding Luer tip on the flow control element. In a preferred, manner, however, the cannula is inserted directly into the flow channel and, for example, glued-in. In a preferred, manner, the flow control element is realized as an injection-molded part. In this case, the cannula can be directly injected-around when the flow control element is injected. For secure fastening, the cannula can extend lengthwise of the entire flow channel, up to the valve face.

The flow control, element can include coupling means for coupling the injection syringe with a further device. The further device can be, for example, a filling device, a transfer device for transferring a fluid or, however, also just a protective cap for receiving a cannula.

In addition, present on the injection syringe can be locking means, in particular in the manner of a bayonet, by way of which the injection syringe is lockable to complementary locking means of a further device. In a preferred manner, the locking means are realized on the basic body. A complementary part of the bayonet-like closure, in this case, is realized in a manner corresponding to the further device. In a preferred manner, the rotation necessary for releasing the locking means is dimensioned in such a manner that, with a corresponding rotation of the closure element in the opposite direction, a transfer from a first control position into a second control position is effected.

Advantageously, the further device includes a protective cap, in particular with a receiving space for receiving a cannula, which protective cap comprises a seat for the coupling means of the flow control element. In this way, the protective cap can be fitted in a simple manner onto the flow control element or can be coupled with it.

The protective cap, in a preferred manner, comprises a connecting piece for the connection of a fluid source and a transfer channel for transferring a fluid from the connecting piece to a mouth opening which is realized on the seat. In this way, the protective cap can, at the same time, fulfill the function of a transfer device which, for filling the injection syringe, is connectable, for example, to a fluid source or to a vial. The outlet opening is preferably realized and arranged on the seat in such a manner that, with coupling means of the flow control element arranged in the seat, there is an, in particular fluid-tight, fluid connection, which is preferably impermeable to germs, between the outlet opening on the seat and the flow channel of the flow control element. The protective cap or the connection piece, in this case, can be realized in such a manner that it is connectable to known systems for transferring a fluid.

Further advantages and individual features of the invention are produced from the following description of several exemplary embodiment and from the figures, in which, in a schematic manner.

Figure 1:
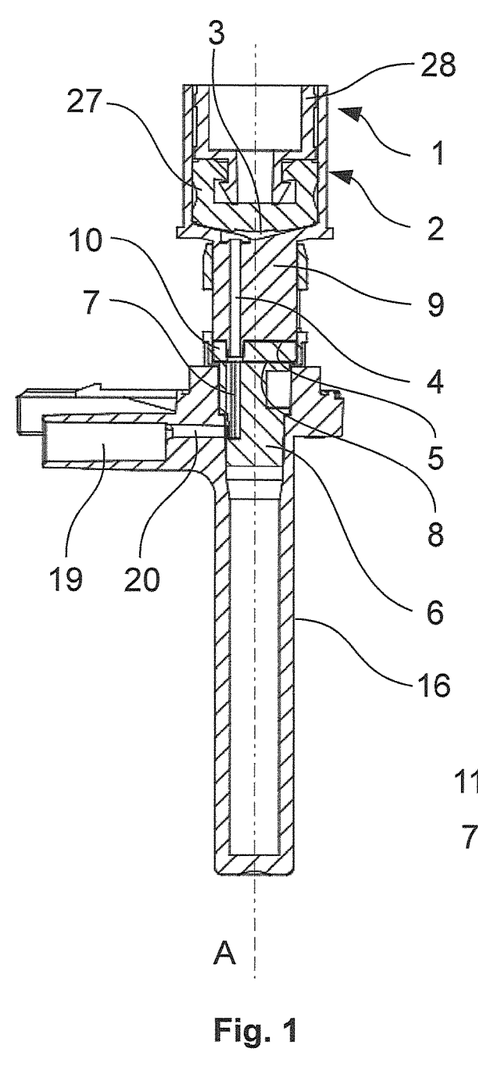
FIG. 1: shows a longitudinal section through a injection syringe according to the invention, where the flow control element is situated in a first control position and a protective cap is fitted thereon.

FIG. 1 shows a longitudinal, section through a injection syringe 1 according to the invention, where a flow control element 6 is situated in a first control, position and a protective cap 16 is fitted, thereon. The injection syringe 1 consists, on the one hand, of a basic body 2 which has a longitudinal axis A and comprises a hollow-cylindrical receiving space 3 for receiving a fluid.

The flow control element 6 comprises two flow channels 7 and 7' (only flow channel 7 is visible in the representation of the longitudinal section). The connection channel 4 on the basic body 2 and the flow channels 7, 7' on the flow control element are in each case aligned parallel to the longitudinal axis A of the basic body 2, but are positioned eccentrically. A piston 27 is arranged so as to be slidable by means of a cylindrical piston rod 28 inside the receiving space 3 of the basic body 2. Adjoining the receiving space 3 is a cylindrically realized head piece 9, through which the connection channel 4 runs. The connection channel 4 is fluidically connected to the interior 3 for receiving the fluid and opens out at the valve face 5 of the basic body 2. A valve face 8 of the flow control element runs parallel to the said valve face 5, a sealing element 10 being arranged between the two plane-parallel valve faces 5 and 8.

Consequently, the connection channel 4 and the flow channel 7 are fluidically connected. The flow channel 7 in the flow control element 6 is additionally connected to a transfer channel 20 on the protective cap 16 which opens out into the connecting piece 19. As a result of actuating the piston rod 28, it is consequently possible to generate negative pressure in the receiving space 3 by way of the piston 27, as a result of which liquid can be drawn from the connecting piece 19 via the transfer channel 20, the flow channel 7 and the flow channel 4 into the receiving space 3.

Figure 2:
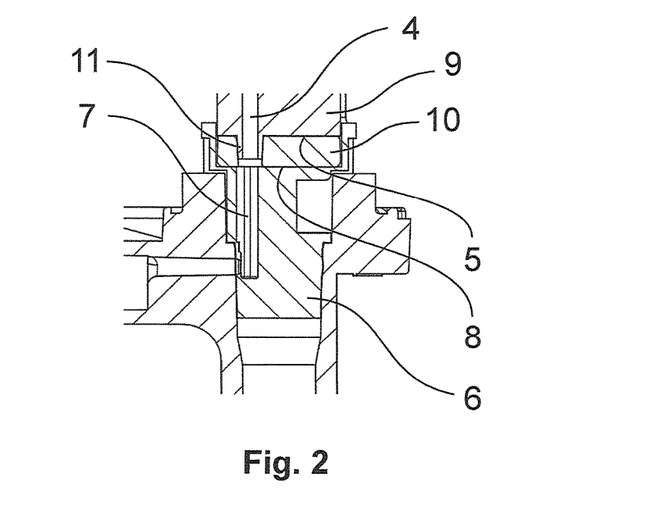
FIG. 2: shows an enlargement of part of the longitudinal section through the injection syringe according to FIG. 1.

FIG. 2 shows an enlargement of part of a longitudinal section through a injection syringe according to the invention according to FIG. 1, the region round the flow control element 6 being shown in more detail. It can be seen that a sealing element 10 is arranged between the valve face 5 of the basic body 2 and the valve face 8 of the flow control element 6. In order to prevent an unwanted relative rotation between the basic body 2 and the sealing element 10, a mouth connecting piece 11, at which the connection channel 4 opens out, is mounted on the head piece 3 of the sealing element 10 on the valve face 5. When the flow control element 6 is rotated, the sealing element 10 consequently rests in a static manner on the valve face 5 of the basic body 2. The fluid connection between the connection channel 4 and the flow channel 7' and the sealing element 10 is also shown in more detail in said figure.

Figure 3:
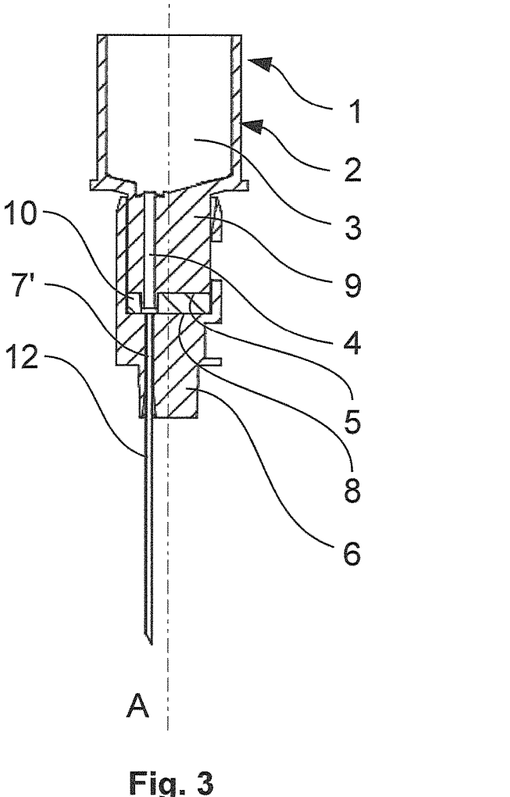
FIG. 3: shows a longitudinal section through the injection syringe according to FIG. 1, the flow control element being situated in a second control position.

FIG. 3 snows the injection syringe 1 according to FIG. 1, the flow control element 6 being moved into a second control position as a result of rotation about a rotational axis which is coaxial with the longitudinal axis A of the basic body 2. It can be seen clearly that an injection cannula 12, which is embedded in a flow channel 7', is located inside the cutting plane as a result of the rotation. In addition, said flow channel 7' is now fluidically connected to the connection channel 4.

As a result of actuating the piston rod 28 and sliding the piston 27 in the direction of the connection channel 4, the contents of the receiving space 3 can be dispensed from the injection syringe 1 via the connection channel 4, the flow channel 7' and the cannula 12.

Figure 4:
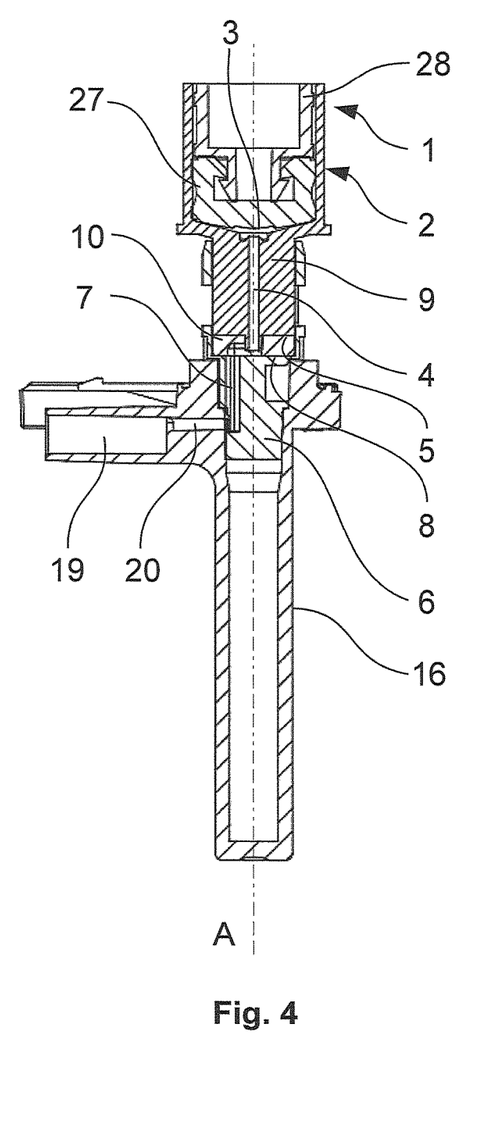
FIG. 4: shows a longitudinal section through an alternative exemplary embodiment of injection syringe according to the invention, the flow control element being situated in a first control position and a protective cap being fitted thereon.
Figure 5:
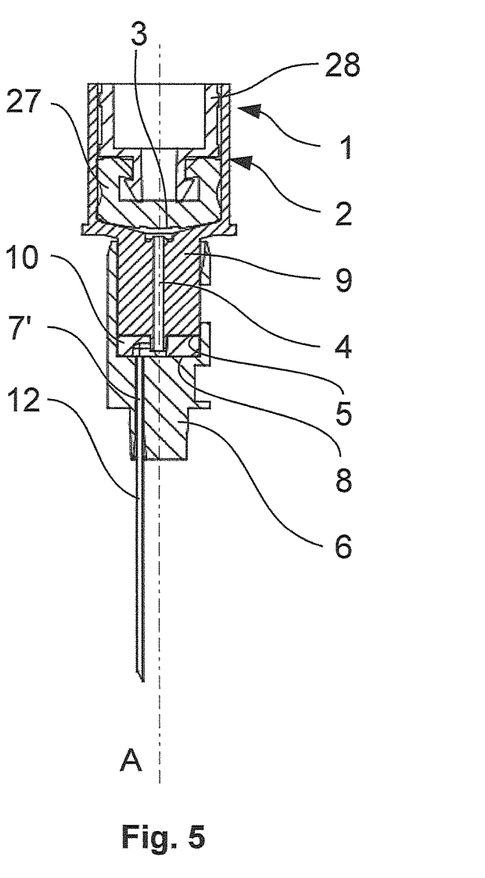
FIG. 5: shows a longitudinal section through the injection syringe according to FIG. 4, the flow control element being situated in a second control position.

FIGS. 4 and 5 show an alternative exemplary embodiment of at injection syringe 1 according to the invention where the connection channel 4 on the basic body 2 is positioned coaxially with the longitudinal axis A thereof. The flow channels 7 and 7' in the flow control element 6, in contrast, are arranged eccentrically in the flow control element 6. In order to produce a fluid connection between the connection channel 4 on the basic body and the flow channels 7 and is on the flow control element 6, the sealing element 10 is developed in such a manner that it forms an indirect liquid path. FIG. 4 shows the injection syringe 1 with the flow control element 6 in a first control position, in which the receiving space 5 of the basic body 2 is able to be filled from the connecting piece 19 via the transfer channel 20, the flow channel 7 and the connection channel 4. In FIG. 5, said same injection syringe can be seen with the flow control element in a second control position, in which the connection channel 4 is connected to the flow channel 7' and the injection cannula 12 in such a manner that it is possible to dispense the fluid out of the receiving space 3.

Figure 6:
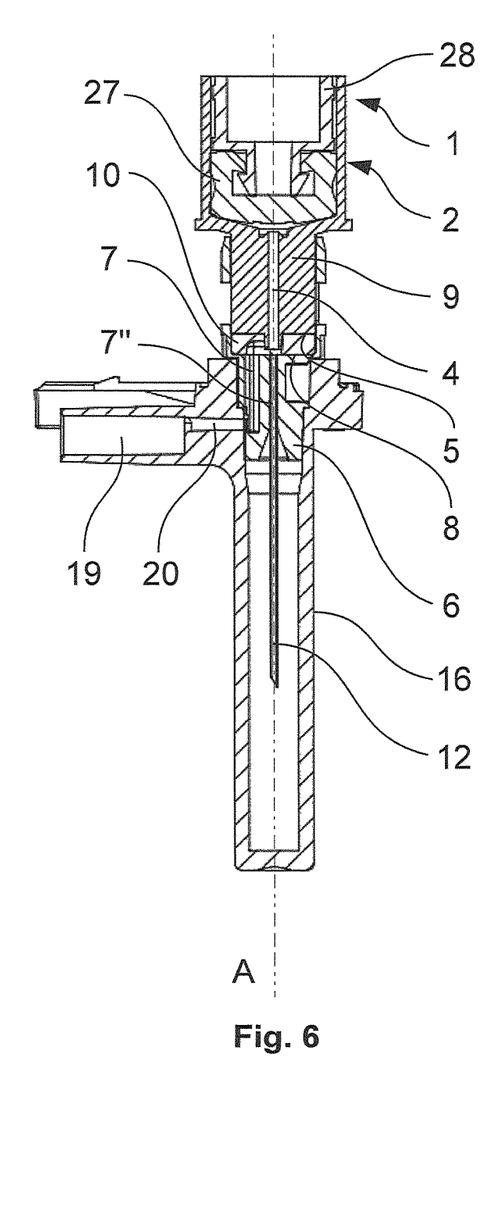
FIG. 6: shows a longitudinal section through a further alternative exemplary embodiment of injection syringe according to the invention, the flow control element being situated in a first control position and a protective cap being fitted thereon.
Figure 7:
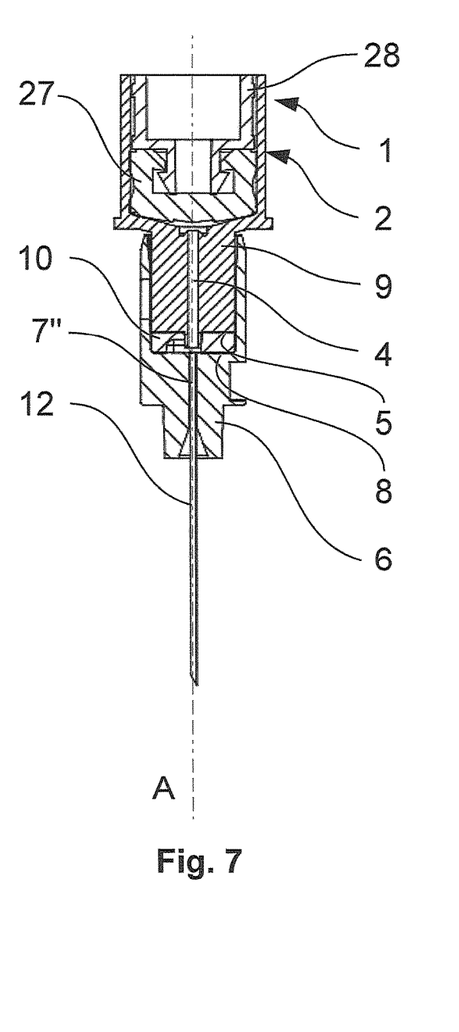
FIG. 7: shows a longitudinal section through the injection syringe according to FIG. 6, the flow control element being situated in a second control position.
Figure 8:
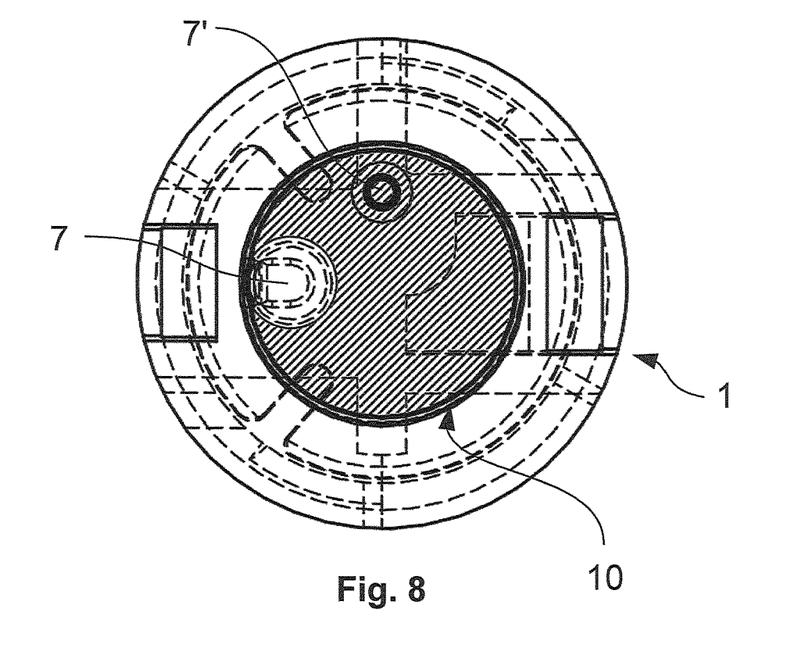
FIG. 8: shows a cross section through the injection syringe according to FIG. 1.
Figure 9:
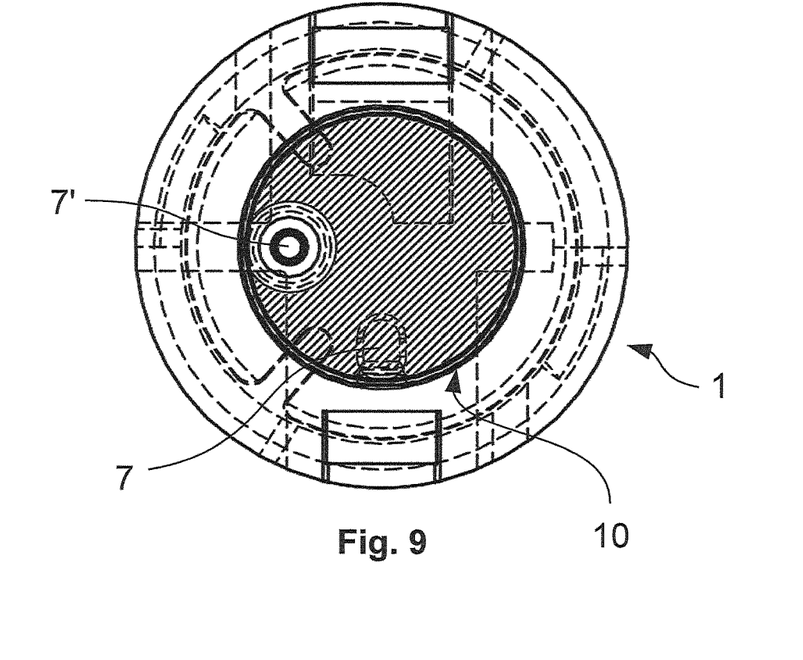
FIG. 9: shows a cross section through the injection syringe according to FIG. 3.
Figure 10:
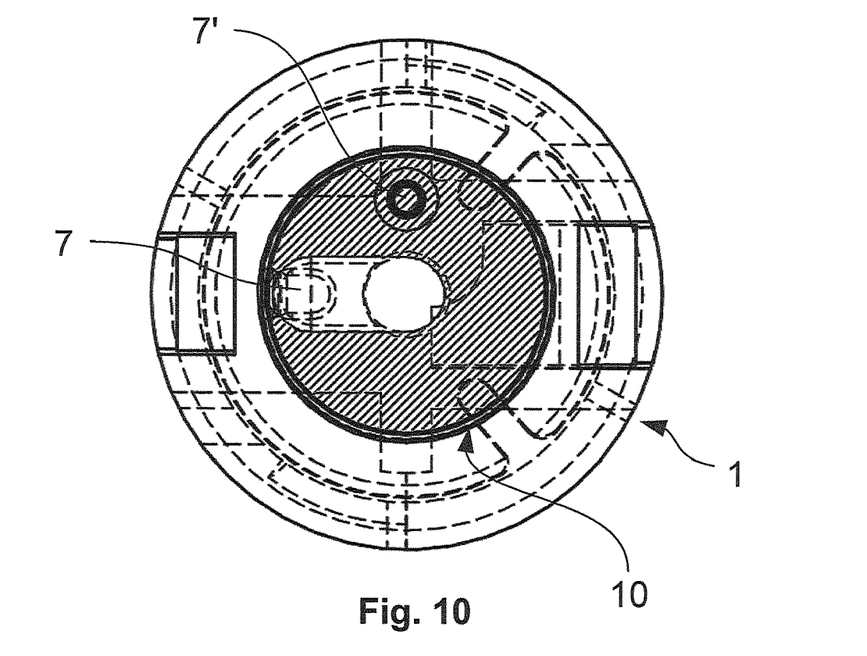
FIG. 10: shows a cross section through the injection syringe according to FIG. 4.
Figure 11:
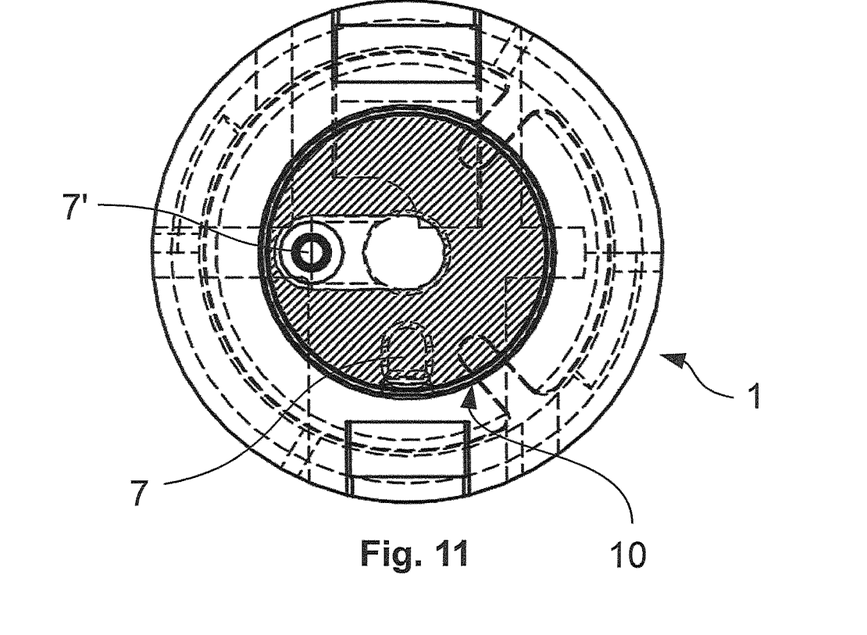
FIG. 11: shows a cross section through the injection syringe according to FIG. 5.
Figure 12:
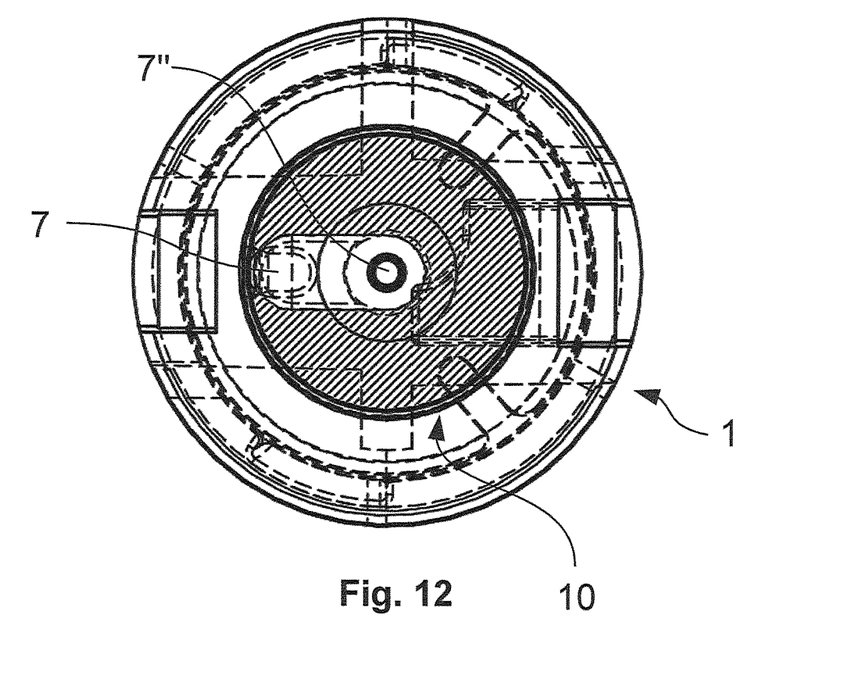
FIG. 12: shows a cross section through the injection syringe according to FIG. 6.
Figure 13:
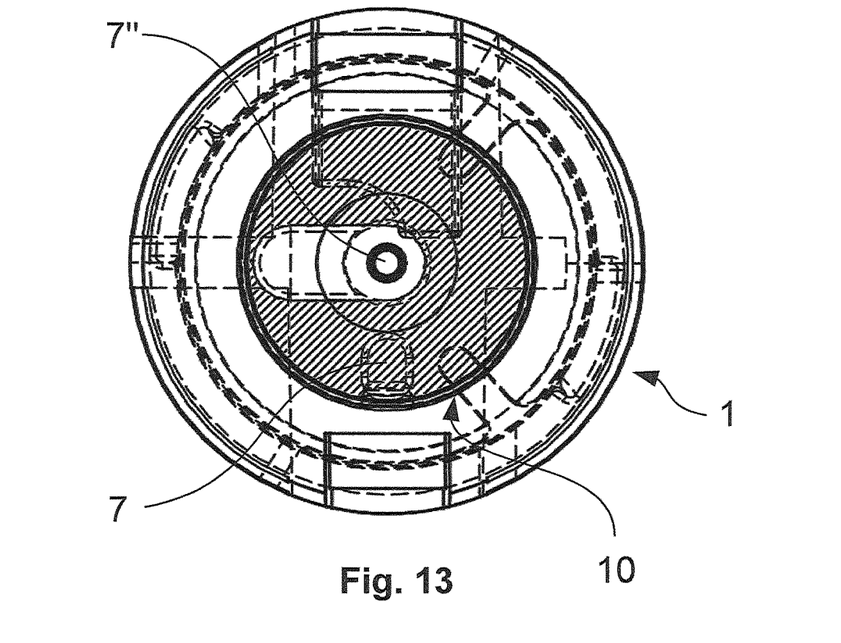
FIG. 13: shows a cross section through the injection syringe according to FIG. 7.

FIGS. 6 and 7 show a further exemplary embodiment of a injection syringe according to the invention where the connection channel 4 on the basic body 2 is realized coaxially with the longitudinal axis A thereof. The flow control element 6 here comprises, in contrast, two flow channels 7 and 7" which are both certainly aligned parallel to the longitudinal axis A of the basic body 2, but 7 is arranged in an eccentric manner and 7' in a coaxial manner. As can be seen in FIG. 6, the sealing element 10 is developed in such a manner that, in a first control position, it produces a fluid connection between the connection channel 4 on the basic body 2 and both flow channels 7 and 7" on the flow control element 6. It is possible to draw liquid into the receiving space 3 of the basic body 2 in said position. The cannula 12 is certainly also fluidically connected to the receiving space 3 but as it is indirectly closed by the protective cap 16, this does not provide any problem regarding filling the injection syringe. FIG. 7 shows the same injection syringe according to the invention with the flow control element 6 in a second position. It can be seen that only the flow channel 7" is still fluidically connected to the connection channel 4 on the basic body 2, the injection cannula 12 being embedded therein. The injection syringe 1 is consequently ready to dispense a liquid.

FIGS. 8 to 13 show cross sections through injection syringes 1 according to FIGS. 1, 3 and 4 to 7. For better clarity, the sealing element 10 is shown, in each case in a hatched manner, it can be seen clearly that depending on the control position of the flow control element 6, different fluid paths between the connection channel 4 (not visible in said figures) and the flow channels 7 and 7' are opened and/or closed. The flow channel 7", in contrast, is always connected to the connection channel 4 (FIGS. 12 and 13) irrespective of the control position of the flow control element 6.

Figure 14:
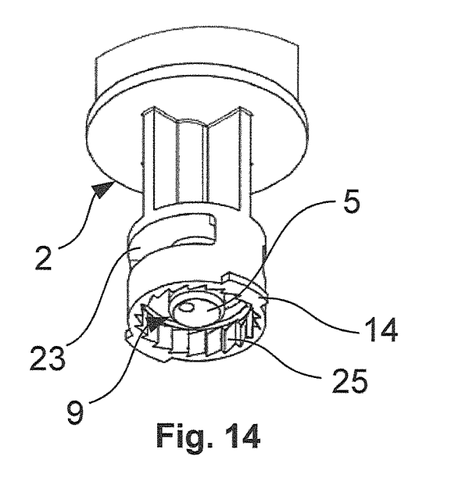
FIG. 14: shows a perspective representation of a basic body of a injection syringe according to the invention.

FIG. 14 shows a perspective representation of a basic body 2 of a injection syringe 1 according to the invention. The head piece 9 with the valve face 5 can be seen clearly. The embodiment shown is also provided with a delimiting device and a blocking device, it only being possible here to see the parts mounted on the basic body 2 (groove 23 and toothing 25). In addition, locking means 14 in the manner of a bayonet closure are mounted on the basic body 2.

Figures 15, 17:
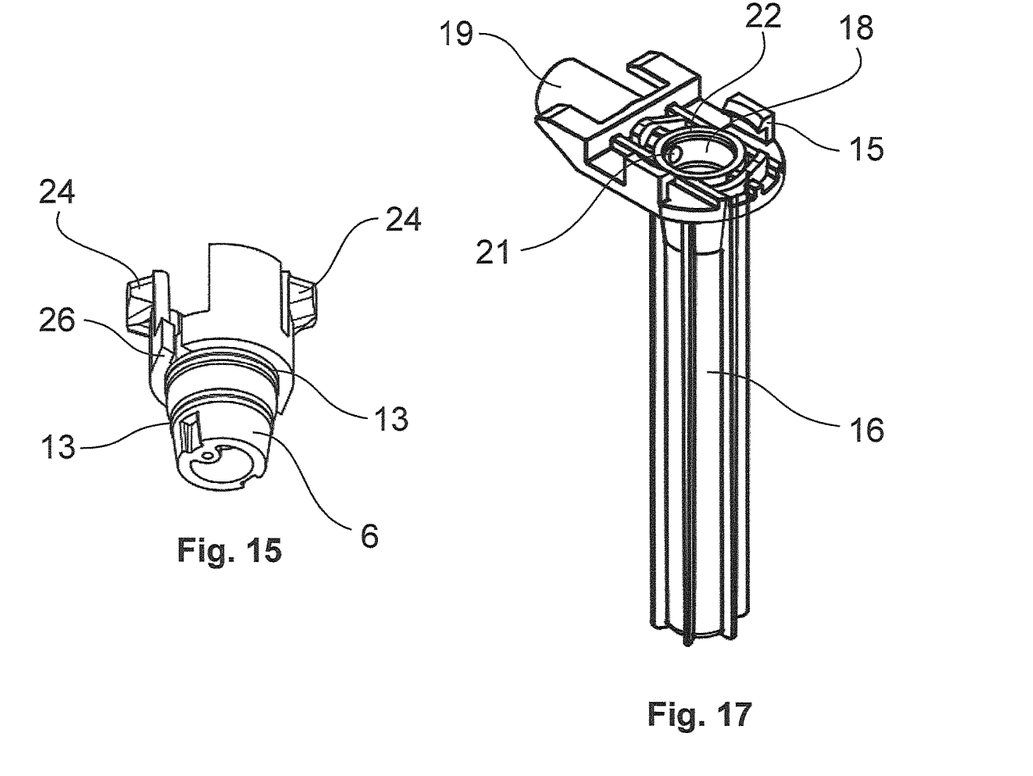
FIG. 15: shows a perspective representation of a flow control element which, is complementary to the basic body according to FIG. 14.
FIG. 17: shows a perspective representation of a protective cap for the injection syringe according to FIG. 16.

FIG. 15 shows a top view of a flow control element 6 consistent with the basic body 2 according to FIG. 14. The engagement elements 24 or the pawls 26 can be seen as part of the delimiting device or the blocking device. In addition, coupling means (intermediate component) 13 are mounted on the flow control element 6.

Figure 16:
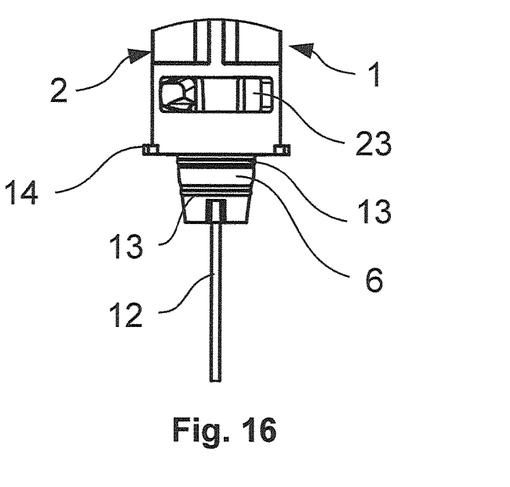
FIG. 16: shows a top view or a injection syringe according to the invention with the components according to FIGS. 14 and 15.

FIG. 16 shows a top view of a injection syringe according to the invention with a basic body according to FIG. 14 and a flow control element according to FIG. 15. It can be seen how the engagement elements 24 engage in the grooves 23 of the delimiting device in order to delimit the rotation of the flow control element 6.

FIG. 17 shows a perspective representation of a protective cap 16 for a injection syringe 1 according to FIG. 16. Said protective cap 16 comprises a seat 18 for the coupling means (intermediate component) 13 mounted on the flow control element 6 as well as own coupling means (intermediate component) 22. A mouth opening 21, which is connected to the connection piece 19 via the transfer channel 20, is also realized on said seat. In addition, the protective cap 16 shown has locking means 15 which are realized in the manner of a bayonet closure.

Figure 18:
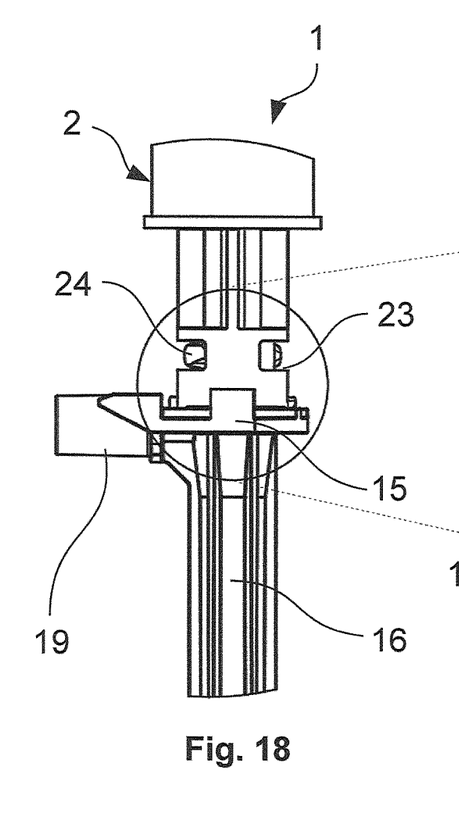
FIG. 18: shows a top view of the injection syringe according to FIG. 16, on which a protective cap according to FIG. 17 is fitted.
Figure 19:
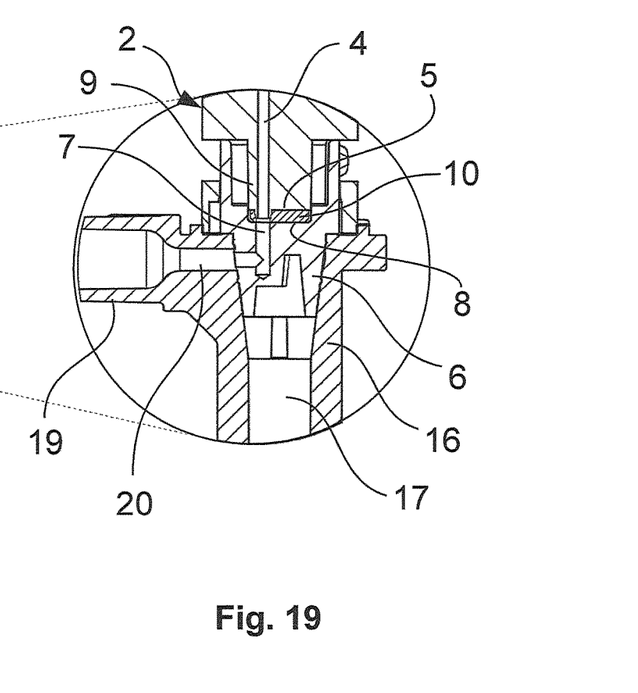
FIG. 19: shows an enlarged section of a part region in the longitudinal direction through the injection syringe with the protective cap according to FIG. 18.

FIG. 18 shows a injection syringe 1 according to the invention according to FIG. 16, on which a protective cap 16 according to FIG. 17 is fitted. FIG. 19 shows a longitudinal section of an enlargement of a part region of FIG. 18. In said detailed representation, it is possible to see the fluid path for filling the device 1 which is formed by the connection piece 19, the transfer channel 20, the flow channel 7 and the flow channel 4. The cavity 17 inside the protective cap 16 can also be seen.

The invention claimed is:

1. An injection syringe for dispensing a fluid, said injection syringe including:
    a) a basic body which has a longitudinal axis and comprises a receiving space for receiving the fluid and a connection channel which communicates with the receiving space, wherein the connection channel opens out at a valve face of the basic body,
    b) a flow control element which is arranged so as to be movable on the basic body and comprises one or several flow channels, and the flow channels open out at a valve face of the flow control element,
    wherein the connection channel of the basic body and the flow channels of the flow control element are directly or indirectly fluidically connected to one another or are movable into fluidic connection as a result of a relative movement of the basic body and the flow control element,
    a sealing element is arranged between the valve face of the basic body and the valve face of the flow control element, a cannula, is arranged or is arrangeable in such a manner on the flow control element that there is a fluid-tight fluid connection to a flow channel, in a preferred manner the cannula is fixedly inserted into the flow channel and is arranged, in particular, parallel to the longitudinal axis (A) of the basic body.

2. The injection syringe according to claim 1, wherein the cannula is fixedly inserted into the flow channel.

3. The injection syringe according to claim 1, wherein the connection channel on the basic body extends parallel to the longitudinal axis of the basic body.

4. The injection syringe according to claim 3, wherein the connection channel on the basic body is arranged eccentrically with reference to the longitudinal axis of the basic body.

5. The injection syringe according to claim 3, wherein the connection channel on the basic body is arranged coaxially with the longitudinal axis of the basic body.

6. The injection syringe according to claim 1, wherein the flow control element is arranged on the basic body so as to be rotatable about a rotational axis which is parallel to the longitudinal axis of the basic body and the flow control element is movable as a result of rotation between several control positions.

7. The injection syringe according to claim 6, wherein at least one flow channel on the flow control element is arranged eccentrically with reference to the longitudinal axis of the basic body.

8. The injection syringe according to claim 6, wherein a flow channel on the flow control element is arranged coaxially with the longitudinal axis of the basic body.

9. The injection syringe according to claim 6, wherein the basic body, on its valve face, comprises at least one element for preventing relative rotation of the basic body and the sealing element.

10. The injection syringe according to claim 9, wherein an element for preventing a relative rotation of the basic body and the sealing element is developed as a mouth connecting piece of the connection channel.

11. The injection syringe according to claim 9, wherein the sealing element is compressible as a result of moving the flow control element from a first control position into a second control position.

12. The injection syringe according to claim 1, wherein an indirect fluid connection is producible via the sealing element between the connection channel of the basic body and at least one flow channel of the flow control element.

13. The injection syringe according to claim 12, wherein by the sealing element, an indirect fluid connection is producible on the flow control element between a connection channel, which is arranged coaxially with the longitudinal axis of the basic body, and at least one flow channel which is arranged eccentrically with reference to the longitudinal axis of the basic body.

14. The injection syringe according to claim 13, wherein along with at least one flow channel arranged eccentrically with reference to the longitudinal axis of the basic body on the flow control element, a further flow channel is present which is connected to the connection channel of the basic body irrespective of the control position of the flow control element.

15. The injection syringe according to claim 14, wherein the further flow channel, which is connected to the connection channel of the basic body irrespective of the control position of the flow control element, is arranged coaxially with the longitudinal axis of the basic body.

16. The injection syringe according to claim 12, wherein by the sealing element, an indirect fluid connection is producible on the flow control element between a connection channel, which is arranged eccentrically with reference to the longitudinal axis of the basic body, and a flow channel which is arranged eccentrically with reference to the longitudinal axis of the basic body.

17. The injection syringe according to claim 12, wherein by the sealing element, an indirect fluid connection is producible on the flow control element between a connection channel, which is arranged eccentrically with reference to the longitudinal axis of the basic body, and a flow channel which is arranged coaxially with the longitudinal axis of the basic body.

18. The injection syringe according to claim 1, wherein the flow control element includes an intermediate component which facilitates coupling the injection syringe to a further device.

19. The injection syringe according to claim 18, wherein a locking means is present on the injection syringe by way of which the injection syringe is lockable to a complementary locking means of a further device.

20. The injection syringe according to claim 18, wherein the further device includes a protective cap, which protective cap comprises a seat for the intermediate component on the flow control element, the protective cap comprises a connecting piece for the connection of a fluid source and a transfer channel for transferring a fluid from the connecting piece to a mouth opening which is realized on the seat, the mouth opening is realized and arranged on the seat in such a manner that, with intermediate component of the flow control element arranged in the seat, a fluid-tight fluid connection is achieved between the mouth opening on the seat and a flow channel of the flow control element.

* * * * *